(12) United States Patent
Hatch et al.

(10) Patent No.: US 9,700,359 B2
(45) Date of Patent: Jul. 11, 2017

(54) LOCKING PLATE WITH SCREW FIXATION FROM OPPOSITE CORTEX

(71) Applicant: Daniel J. Hatch, Greeley, CO (US)

(72) Inventors: Daniel J. Hatch, Greeley, CO (US); Brandon Beckendorf, Carrollton, TX (US)

(73) Assignee: Daniel J. Hatch, DPM, Greeley, CO (US)

( * ) Notice: Subject to any disclaimer, the term of this patent is extended or adjusted under 35 U.S.C. 154(b) by 582 days.

(21) Appl. No.: 13/781,492

(22) Filed: Feb. 28, 2013

(65) Prior Publication Data

US 2013/0226248 A1   Aug. 29, 2013

Related U.S. Application Data

(60) Provisional application No. 61/614,909, filed on Mar. 23, 2012.

(51) Int. Cl.
| | |
|---|---|
| *A61B 17/88* | (2006.01) |
| *A61B 17/80* | (2006.01) |
| *G06K 9/00* | (2006.01) |

(52) U.S. Cl.
CPC .......... *A61B 17/80* (2013.01); *A61B 17/8033* (2013.01); *G06K 9/00671* (2013.01)

(58) Field of Classification Search
None
See application file for complete search history.

(56) References Cited

U.S. PATENT DOCUMENTS

| | | |
|---|---|---|
| 2005/0033430 A1 | 2/2005 | Powers et al. |
| 2007/0191848 A1 | 8/2007 | Wack et al. |
| 2009/0234462 A1* | 9/2009 | Mullaney ........... A61B 17/8061 623/47 |
| 2010/0125300 A1 | 5/2010 | Blitz et al. |
| 2011/0137351 A1 | 6/2011 | Huebner et al. |
| 2012/0265204 A1 | 10/2012 | Schmierer et al. |
| 2014/0277176 A1 | 9/2014 | Buchanan et al. |

\* cited by examiner

*Primary Examiner* — Sameh Boles
(74) *Attorney, Agent, or Firm* — Fredrikson & Byron, P.A.

(57) ABSTRACT

An apparatus for supporting a bone includes a plate configured for positioning on a tension side of the bone. Two or more fasteners are configured to extend from an opposite side of the bone to the plate, and engage the plate after extending through the bone. The plate has an attachment mechanism operable to engage with the fasteners. In other aspects, a method of performing a surgical procedure includes positioning a plate on a tension side of a bone, and forming a hole from an opposite side of the bone to the plate. A fastener is inserted through the hole to the plate, and the plate is adjusted into position on the bone surface on the tension side of the bone. One or more additional holes are formed from the opposite side of the bone to the plate, and one or more additional fasteners are inserted.

19 Claims, 11 Drawing Sheets

FIG. 18

LOCKING PLATE WITH SCREW FIXATION FROM OPPOSITE CORTEX

CROSS-REFERENCE TO RELATED APPLICATIONS

The present application claims priority to U.S. Provisional Patent Application No. 61/614,909, entitled "PLANTAR LOCKING PLATE WITH SCREW FIXATION FORM OPPOSITE CORTEX," filed Mar. 23, 2012, the disclosure of which is hereby incorporated herein by reference in its entirety.

TECHNICAL FIELD

The present application relates to devices for supporting a bone in a human foot or hand, and relates in particular to a locking plate for positioning on the tension side of bone.

BACKGROUND

Plating technology has reached its 4th generation, evolving to locking plate constructs. This system provides little to no contact with the bone, thus preserving blood supply and the periosteum. The screw to plate construct provides a fixed angle, yielding more stability and resistance to pull out.

From a mechanical standpoint, the plate is best utilized and functions the best when placed on the tension side of the bone. In case of foot surgery, this is most often on the plantar surface. Additionally, this construct may facilitate improved healing and earlier weight bearing.

Current systems in foot and ankle surgery include plates or supporting structures that are utilized or located dorsally and on the sides of the bone, primarily due to anatomical constraints. While the plate can be placed plantarly, difficulties arise when placing screws from the bottom as designed. This difficulty stems from the concentration of neurovascular structures on the tension side of the bone and surgical exposure. Furthermore, in current systems, the head of the screw will attach to the plate. This attachment technique requires undesirable dissection and/or exposure of the arteries and nerves on the tension side of the bone.

BRIEF SUMMARY

The present application provides for methods and apparatuses for supporting a bone (e.g. a bone in a human foot or hand). In some aspects, an apparatus for supporting a bone includes a plate configured for positioning on a tension side of the bone. Two or more fasteners are configured to extend from an opposite side of the bone to the plate, and engage the plate after extending through the bone. The plate has an attachment mechanism operable to engage with the fasteners. In other aspects, a method of performing a surgical procedure includes positioning a plate on a tension side of a bone, and forming a hole from an opposite side of the bone to the plate. A fastener is inserted through the hole to the plate, and the plate is adjusted into position on the bone surface on the tension side of the bone. One or more additional holes are formed from the opposite side of the bone to the plate, and one or more additional fasteners are inserted.

The foregoing has outlined rather broadly the features and technical advantages of the present invention in order that the detailed description that follows may be better understood. Additional features and advantages will be described hereinafter which form the subject of the claims. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of embodiments described herein, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present embodiments.

BRIEF DESCRIPTION OF THE DRAWINGS

For a more complete understanding, reference is now made to the following descriptions taken in conjunction with the accompanying drawings, in which.

DETAILED DESCRIPTION

Figure 1A:
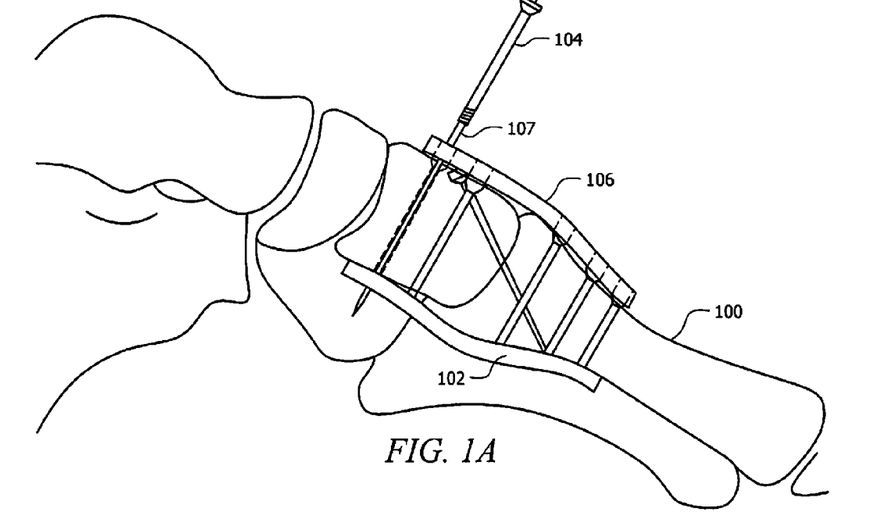
FIG. 1A provides a view of a side of a foot bone having a plate and screws engaged therewith using a template and guide pin according to an aspect of the present disclosure.
Figure 1B:
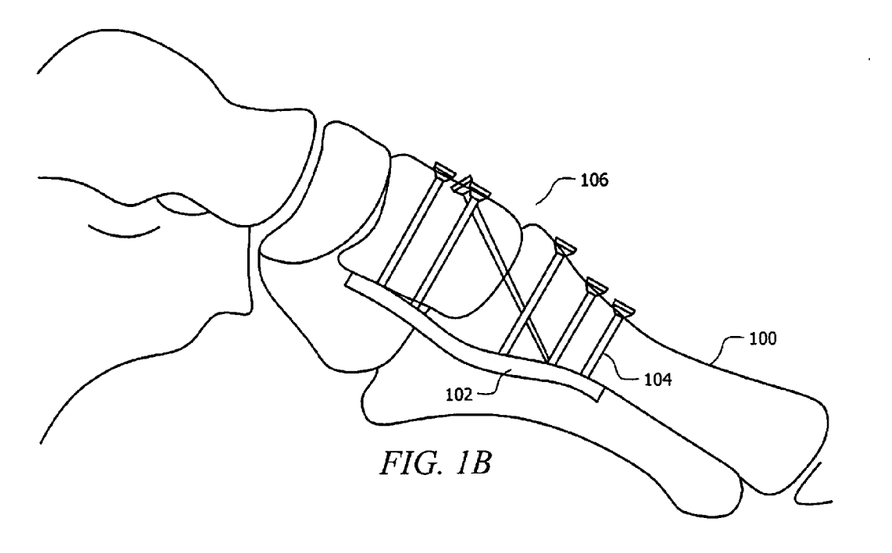
FIG. 1B provides a view of a side of a foot bone having a plate and screws engaged therewith according to an aspect of the present disclosure.

Referring generally to FIGS. 1A and 1B, a new device is disclosed for supporting a bone 100 (e.g. a bone in a human foot or hand). The device includes a locking plate 102 that is placed at a tension side of the bone 100 and that is attached to the bone by two or more fasteners 104 (e.g., special screws) placed into the bone 100 from a side opposite the locking plate 102. While it is envisioned that some or all of the fasteners 104 may extend directly from the side opposite the locking plate, it is also envisioned that some or all of the fasteners 104 may extend at various angles from the side opposite the locking plate 102. Stated differently, the fasteners 104 need not be perpendicular to a longitudinal axis of the locking plate, and may extend from any region of the bone 100 that is opposite the tension bearing side of the bone 100. Additionally, it is envisioned that one or more heads of the fasteners 104 may protrude (e.g., entirely or partially) above the surface of bone 100, may be flush with the surface of the bone 100, or may be embedded into the bone 100 so as to reside sunk beneath the surface of the bone 100.

In the case of an application to a foot, the locking plate 102 is placed plantarly, and the fasteners 104 are applied dorsally (i.e., from the opposite cortex). These fasteners 104 engage with and lock to the plate 102 after extending through the bone 100. In some aspects, the plate 102 may have threaded openings, or another attachment mechanism, to receive and engage with the fasteners 104. As will be further detailed below, a fixation screw may be used proximally at the fusion site during a surgical procedure. Then a guide pin 107 may be employed with an optional template 106 during a surgical procedure to aid in forming holes through the bone to the threaded openings or other attachment mechanism.

The guide pin 107 may be a cylindrically shaped, elongated member having a pointed tip at one or both ends. The pointed tip may be manufactured in such a way that it is self-drilling. Example tips for guide pins are trochar and diamond tips. It is envisioned that a guide pin 107 may be composed of titanium, stainless steel, or any other suitable biocompatible material.

The guide pin 107 may be driven through the bone 100 to assist in correct placement of the drill and/or fastener 104, such as a locking screw. A cannulated (e.g., having a bore therethrough) drill may be placed over the guide pin 107 to drill a void for the fastener 104. If the fastener 104 is also cannulated, the guide pin may be left in place to assist in inserting the fastener 104 over the guide pin 107, through the void, and into the locking plate 102. If the fastener 104 is not cannulated, then the guide pin 107 may be removed prior to inserting the fastener 104.

It is noted that while much of the following description discusses embodiments which utilize plates and screws configured to be located in a patient's foot (e.g. plantar plates and the like), the inventive concepts described herein may be applied to various types of plates manufactured in various sizes. Further, plates may be designed for placement on many different portions of the body where it may be helpful to utilize screws which affix a plate from the opposite cortex of the respective bone placement.

As described in greater detail below, in order to facilitate the plantar plate and ease of use, the screw design may include the tip of the screw having the locking threads and the head of the screw having the compression smooth design or threaded design for osseous purchase (engagement with the bone). It is envisioned that the system may be made out of stainless steel or titanium or titanium alloy. It is also envisioned that one or more components may be made of a dissolvable material. It is additionally envisioned that the system may be solid core or cannulated. It is further envisioned that the system e.g., screw) may be composed of two parts that merge together.

The plantar plate may have threads accepting the screw from the opposite cortex (e.g. the opposite hemisphere of the bone) versus present designs screwing in from the same cortex. The screws may have a normal thread pattern reversed. For example, the locking threads may be on the tip of the screw and the threads for bone purchase (i.e., attachment) may be more on the shank and head of the screw.

This system may incorporate common sizes of screws and plates utilized for the intended anatomic part. For example, diameter sizes (in mm) of 2.7, 3.0, 3.5 and 4.0 may be included. These screws may then range in length from 12-50 mm as described in greater detail below. As mentioned above, it is envisioned that the screws may be either be cannulated or solid core.

Figure 2:
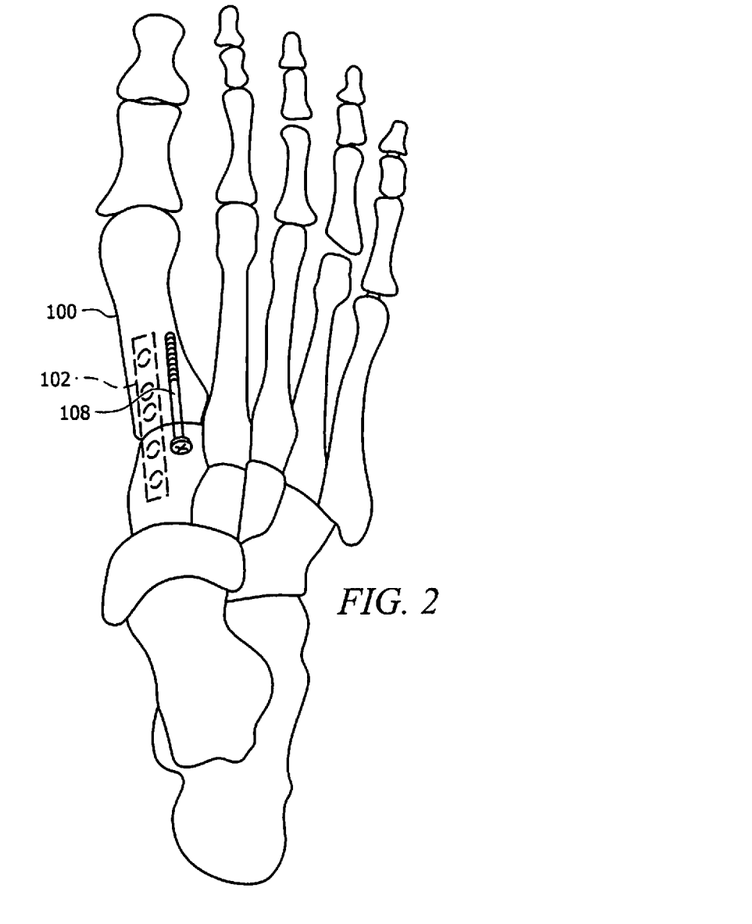
FIG. 2 provides a view of a dorsal side of a foot bone having a plate and screws engaged therewith according to an aspect of the present disclosure.

Referring now to FIG. 2, prior to utilization of the guide pin, a fixation screw 108 may be applied proximally at the fusion site to join pieces of bone 100 together. A locking plate 102 may then be positioned on a tension side of the bone 100, and a guide pin may be employed with a template 106 to aid in forming a first hole through the bone 100 using, for example, a cannulated drill, as described above. Then, a fastener 104 may be inserted through the hole and engaged with a threaded opening of locking plate 102, or other attachment mechanism. Additionally, in some embodiments, after the first fastener 104 is inserted, the placement of locking plate 102 may be adjusted (e.g. rotated into position, etc.) on the tension side of the bone 100, and one or more additional holes and fasteners 104 may be formed and inserted, respectively.

In some aspects, the locking plate 102 may be configured to engage only with the two or more fasteners 104 extending from the opposite side of the bone 100. This configuration greatly reduces dissection and exposure of neural and vascular tissue in accessing the tension side of the bone. In other aspects, the locking plate 102 may be configured to engage with additional fasteners from the same side or another side of the bone 100. These other configurations still achieve reduction of dissection and exposure of the neural and vascular tissue in accessing the tension side of the bone 100.

Figure 3:
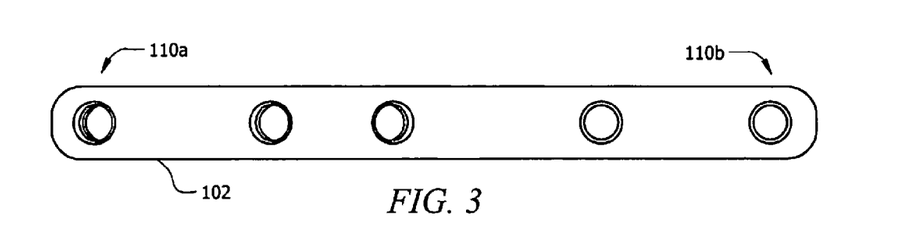
FIG. 3 provides a plan view of a locking plate according to an aspect of the present disclosure.

Turning now to FIG. 3, the locking plate 102 may be configured as an elongated member having an attachment mechanism, such as two or more threaded openings, e.g. 110A and 110B. In some implementations, the openings may be smooth through holes for use with bolts instead of screws. It should be understood that the dimensions of the locking plate may vary depending on the location of plate 102 within a patient, the areas/bones which are being treated, the size of the patient, etc.

Figure 4:
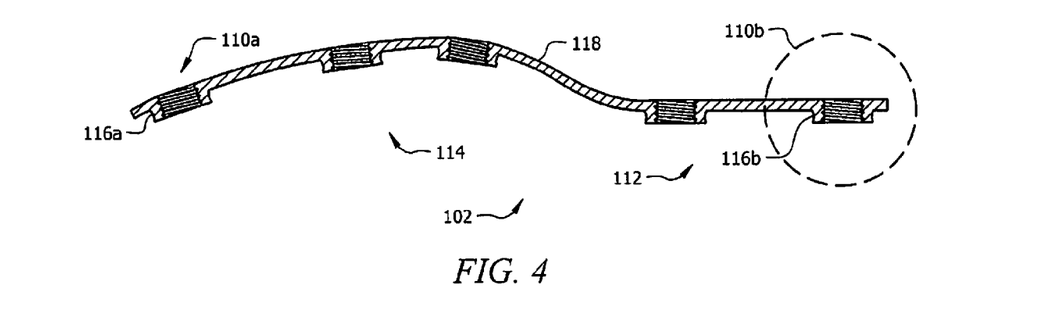
FIG. 4 provides a cross-sectional view of the locking plate of FIG. 3.
Figure 5:
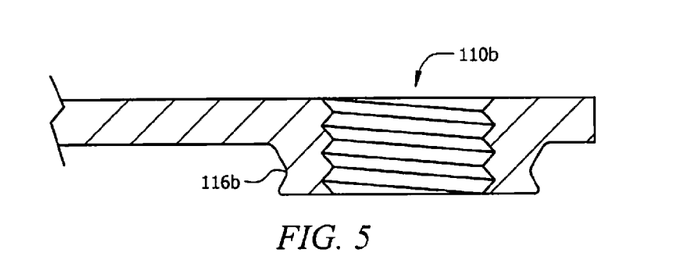
FIG. 5 provides a detail of FIG. 4.
Figure 6:
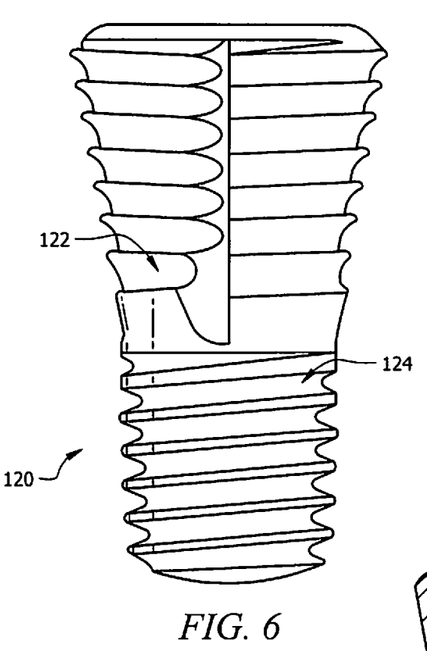
FIG. 6 provides an isometric view of a locking screw according to an aspect of the present disclosure.
Figure 7:
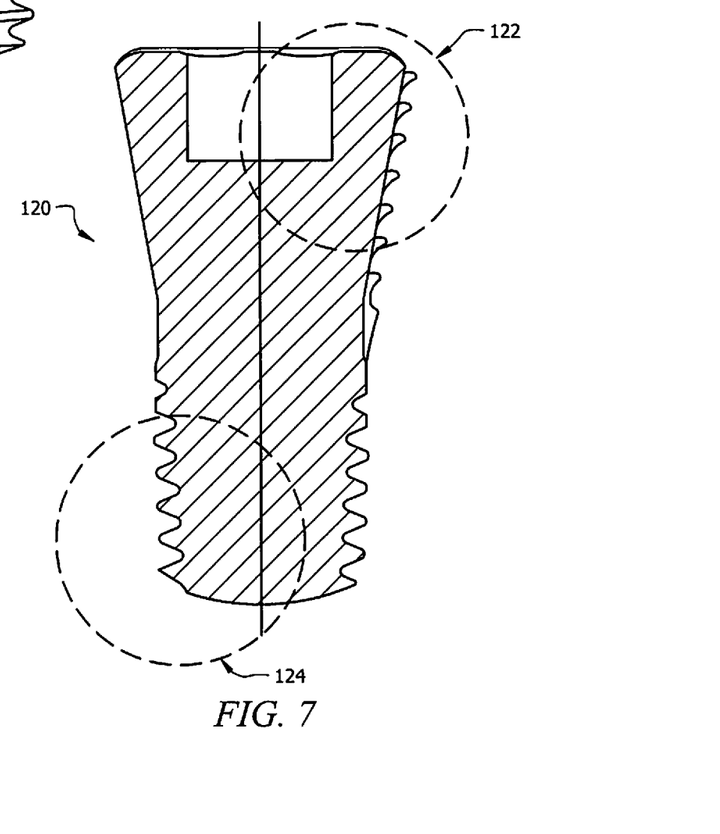
FIG. 7 provides a cross-sectional view of the locking screw of FIG. 6.
Figure 8:
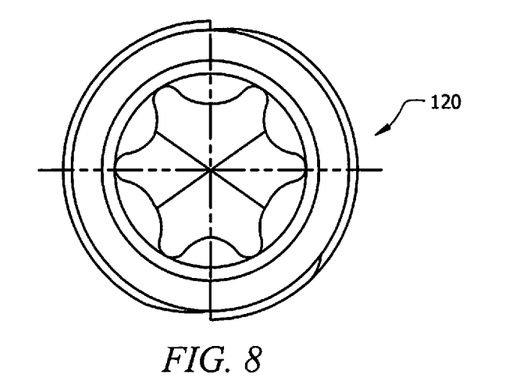
FIG. 8 provides a plan view of the locking screw of FIG. 6.
Figure 9:
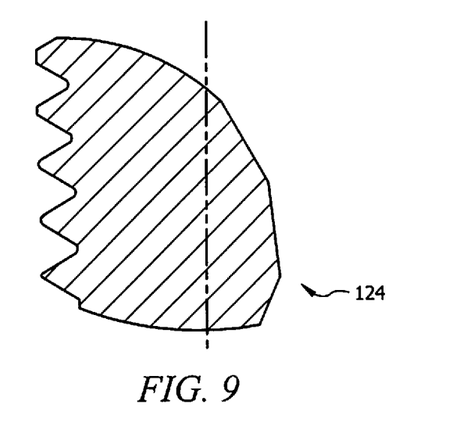
FIG. 9 provides a detail of FIG. 6.
Figure 10:
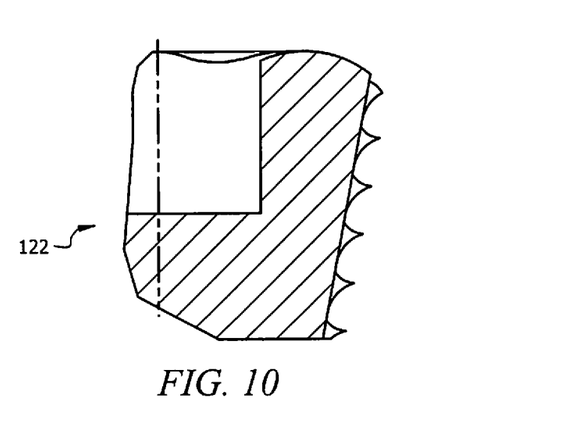
FIG. 10 provides another detail of FIG. 6.
Figure 11:
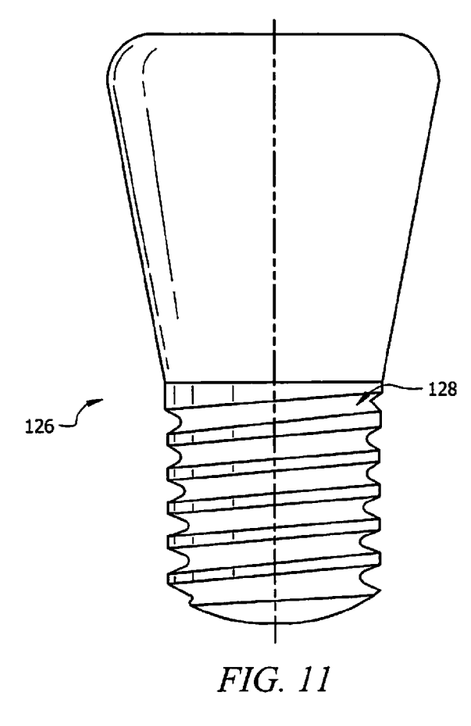
FIG. 11 provides an isometric view of a compression screw according to an aspect of the present disclosure.
Figure 12:
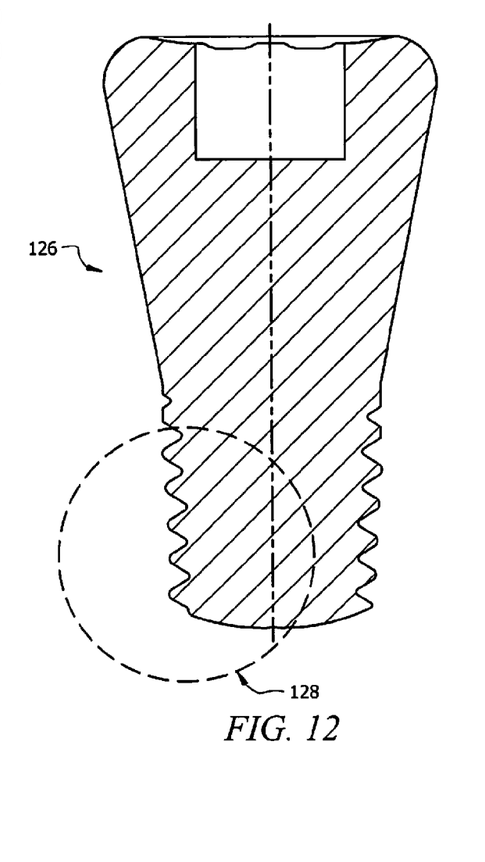
FIG. 12 provides a cross-sectional view of the compression screw of FIG. 11.
Figure 13:
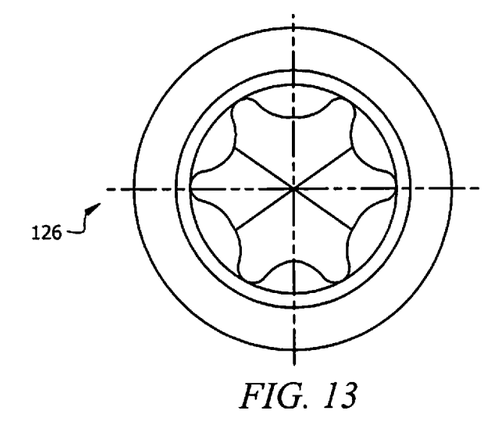
FIG. 13 provides a plan view of the compression screw of FIG. 11.
Figure 14:
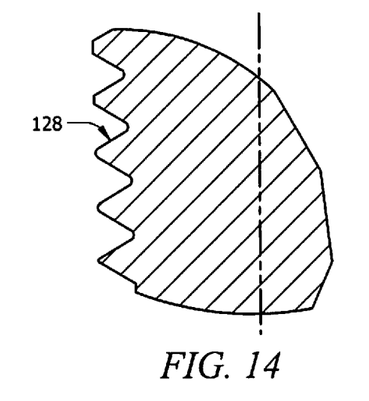
FIG. 14 provides a detail of FIG. 12.

Referring to FIG. 4, the locking plate 102 may be configured to be linear, to have a curvature, or to have a combination of both linear regions 112 and curved regions 114. Such variations will generally vary based on the location of plate 102 within a patient, the areas/bones which are being treated, the size of the patient, etc. Locking plate 102 may further be configured with raised surfaces 116A and 116B respectively provided at openings 110A and 110B enable lengthening of thread of the threaded openings 110A and 110B. The lengthened thread provides additional engagement regions, while raised surfaces 116A and 116B permit the locking plate to be thinner at one or more regions 118 at which threaded openings 110A and 110B are absent.

The following figures illustrate multiple embodiments of screws which are configured to secure a locking plate to a surface of a bone, wherein one or more screws are configured to screw into the locking plate originating from the opposite cortex. It is appreciated that such screws may be implemented in many manners. For example, a screw may be configured to be threaded to be received within threads of the locking plate. Further, a screw may be configured such that the threads will allow for additional locking within the plate. Screws may additionally have a top portion which comprises one or more portions which secure the screw against a bone, e.g. a threaded portion, a screw head and the like.

It is also appreciated that and one of skill in the art will recognize that fastening a plate from an opposite cortex may be implemented with a fastening means other than a screw. For example, it is envisioned that bolts may be employed as the fasteners. Additionally, a fastener may be any other elongated member which may be secured to a plate with one or more of an anchor, friction fit, snap fastener, etc. In some implementations, it is envisioned that the fasteners may be comprised of one or two piece components.

Turning now to FIGS. 6-10 and referring generally thereto, a locking screw 120 for use with the locking plate described above may have locking threads 124 on a tip of the screw. These locking threads 124 are configured to engage with the thread pattern of the two or more openings of a locking plate. The locking screw 120 may also have threads 122 for bone purchase. These threads 122 for bone purchase may be located on a head and shank region of the screw. It should be understood that the locking screw 120 illustrated in FIGS. 6-10 may be a compressed version of the locking screws depicted in FIG. 15.

Turning now to FIGS. 11-14 and referring generally thereto, a compression screw 126 for use with the locking plate described above may have locking threads 128 on a tip of the screw. These locking threads 128 are configured to engage with the thread pattern of the two or more openings. In contrast to the locking screw described above, the compression screw 126 may have a head and shank region devoid of threads.

Figure 15:
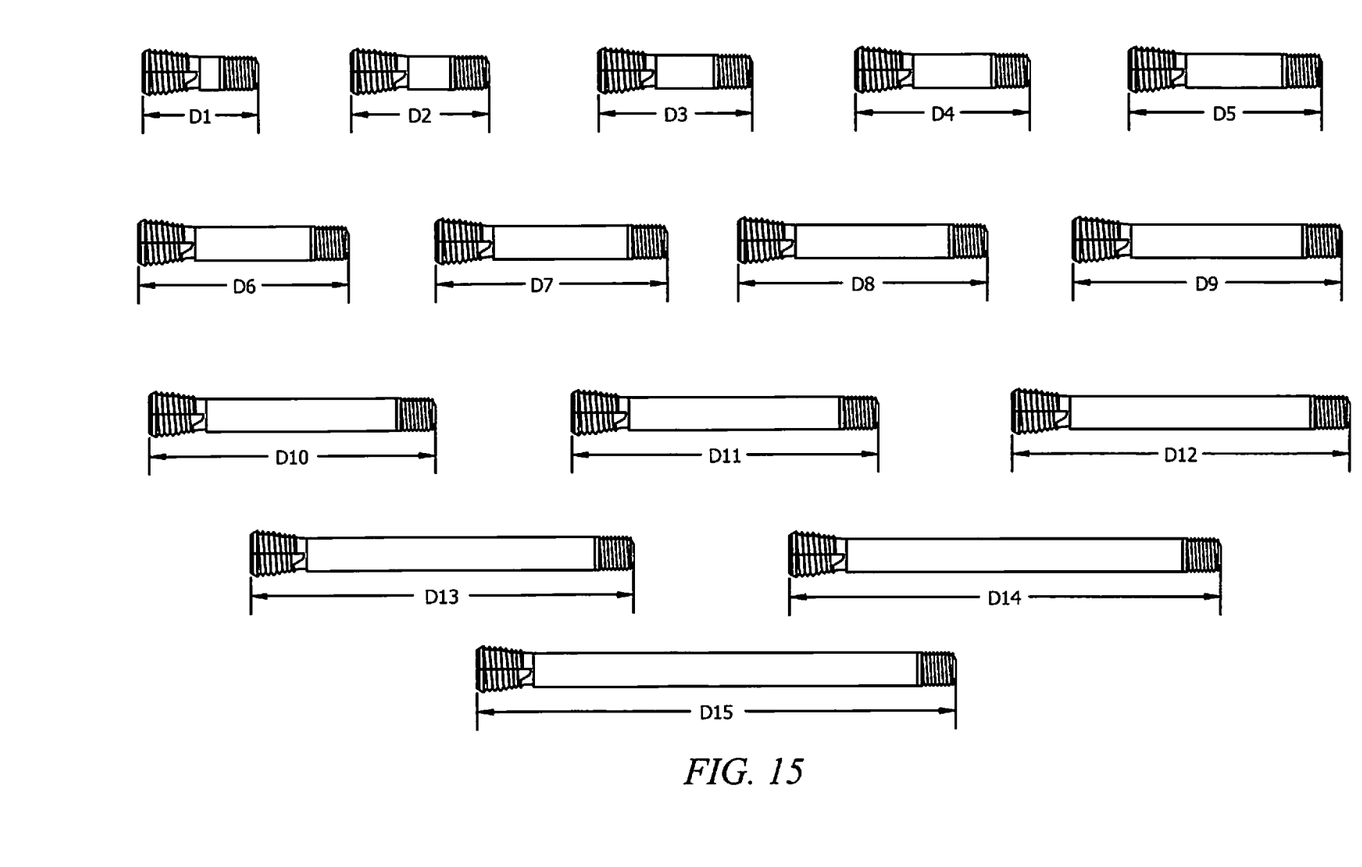
FIG. 15 provides views of locking screws of various lengths in accordance with an aspect of the present disclosure.

Turning now to FIG. 15, a variety of example lengths are shown for the locking screw. Example lengths include a dimension D1 of fifteen millimeters, a dimension D2 of fourteen millimeters, a dimension D3 of sixteen millimeters, a dimension D4 of eighteen millimeters, a dimension D5 of twenty millimeters, a dimension D6 of twenty-two millimeters, a dimension D7 of twenty-four millimeters, a dimension D8 of twenty-six millimeters, a dimension D9 of twenty-eight millimeters, a dimension D10 of thirty millimeters, a dimension D11 of thirty-two millimeters, a dimension D12 of thirty-six millimeters, a dimension D13 of forty millimeters, a dimension D14 of forty-five millimeters, and a dimension D15 of fifty millimeters. However, it should be readily understood that other lengths may be provided.

Figure 16:
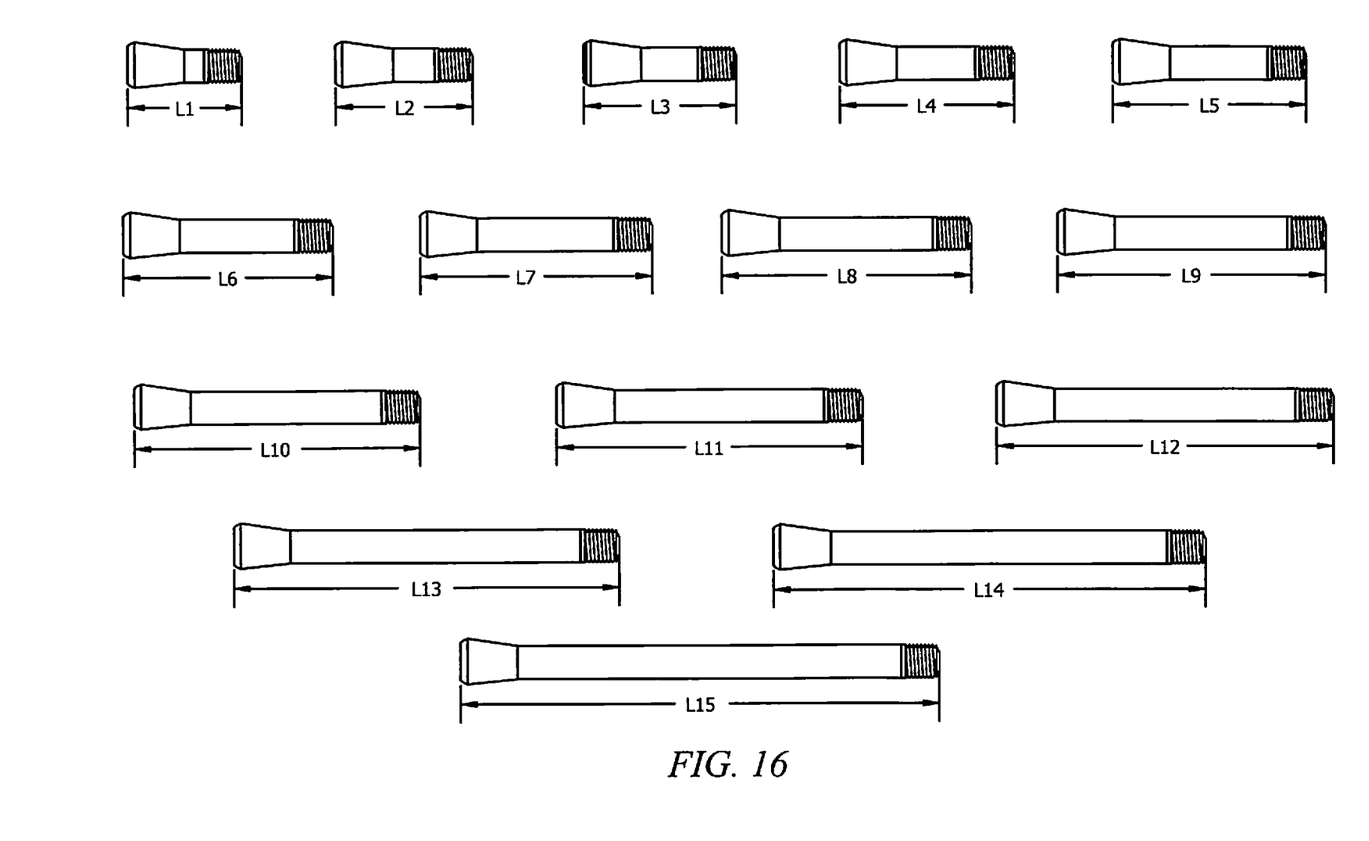
FIG. 16 provides views of compression screws of various lengths in accordance with an aspect of the present disclosure.

Turning now to FIG. 16, a variety of example lengths are shown for the compression screw. Example dimensions include a length L1 of fifteen millimeters, a length L2 of fourteen millimeters, a length L3 of sixteen millimeters, a length L4 of eighteen millimeters, a length L5 of twenty millimeters, a length L6 of twenty-two millimeters, a length L7 of twenty-four millimeters, a length L8 of twenty-six millimeters, a length L9 of twenty-eight millimeters, a length L10 of thirty millimeters, a length L11 of thirty-two millimeters, a length L12 of thirty-six millimeters, a length L13 of forty millimeters, a length L14 of forty-five millimeters, and a length L15 of fifty millimeters. However, it should be readily understood that other dimensions may be provided.

Figure 17:
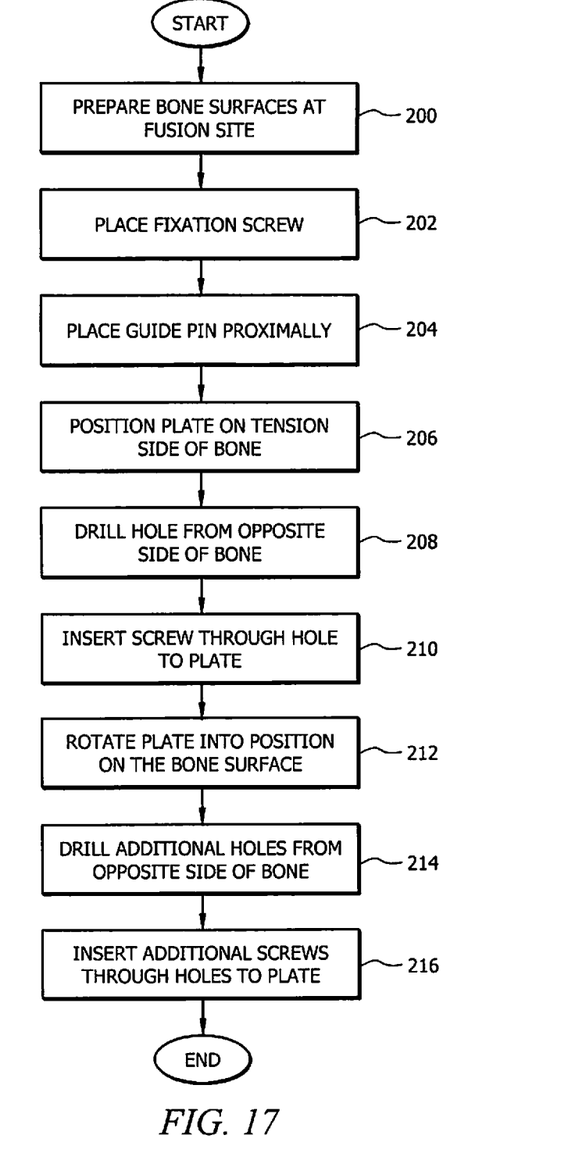
FIG. 17 provides a flow diagram illustrating a method of performing a surgery procedure according to an aspect of the present disclosure.
Figure 18:
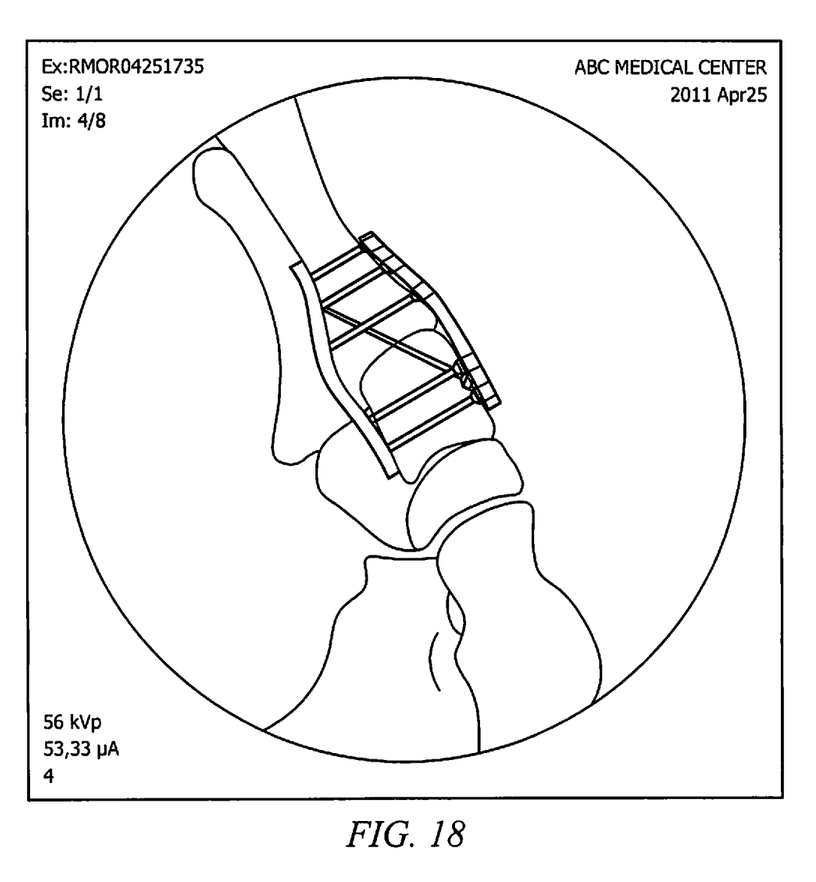
FIG. 18 provides a graphical illustration of results of a surgical procedure performed according to the method of FIG. 17.

Turning now to FIG. 17 and FIG. 18 and referring generally thereto, the surgical procedure described above is now described and an inserted device is illustrated in further detail. It is noted that embodiments may utilize or omit one or more of the outlined steps. Additionally, it is noted that one or more steps may be implemented in a different order.

At step 200, a fusion site (i.e., where two pieces of bone are to be joined together) may be prepared in standard fashion. At step 202, a fixation screw of surgeon preference may be placed to oppose or connect the fusion site and fix in desired alignment. At step 204, a guide pin may be placed proximally. At step 206, the plate may be placed with evaluation by image intensification or fluoroscopy. At step 208, a drill corresponding to the guide pin may be used with a depth gauge, and then cannulated locking screw placement at step 210. At step 212, the plate may be adjusted in place (i.e., positioned in the correct anatomical alignment) with image assessment. At steps 214 and 216, the distal screw may be placed in the same fashion. Any remaining holes may similarly be addressed individually. Locking screws can be used or in desired instances, compression screws can be used. Standard post-operative care may also be provided.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of performing a surgical procedure, the method comprising:
    positioning a plate on a plantar side of a bone in a foot;
    forming a hole from a dorsal side of the bone to the plate;
    inserting a fastener through the hole to the plate;
    adjusting the plate into position on a bone surface on the plantar side of the bone;
    forming one or more additional holes from the dorsal side of the bone to the plate; and
    inserting one or more additional fasteners through the one or more additional holes to the plate.

2. The method of claim 1, wherein the plate has an attachment mechanism operable to engage with the fastener and the one or more additional fasteners extending from the opposite side of the bone.

3. The method of claim 2, wherein the fastener and the one or more additional fasteners correspond to a screw and one or more additional screws having locking threads on tips thereof that are configured to engage with two or more threaded openings of the attachment mechanism.

4. The method of claim 3, wherein the screw and the one or more additional screws are at least one of cannulated or solid bore.

5. The method of claim 3, wherein the screw and the one or more additional screws have threads for bone purchase.

6. The method of claim 5, wherein the threads for bone purchase are located on a head and shank region of the screw and the one or more additional screws.

7. The method of claim 1, wherein the plate is configured to engage only with the fastener and the one or more additional fasteners extending from the opposite side of the bone.

8. The method of claim 1, further comprising preparing joint surfaces of the bone.

9. The method of claim 1, further comprising:
placing a fixation screw through the bone; and
positioning the plate on the plantar side of the bone.

10. The method of claim 1, further comprising employing a guide pin to aid in forming the one or more additional holes.

11. The method of claim 1, wherein forming the hole and forming the one or more additional holes includes employing a cannulated drill to drill the hole and the one or more additional holes.

12. The method of claim 1, further comprising employing an additional fixation mechanism, including at least one of: additional fasteners not engaged with the plate; or an additional plate.

13. The method of claim 12, wherein employing an additional plate includes employing a double plate to support the opposite side of the bone.

14. A method of performing a surgical procedure, the method comprising:
positioning a plate having an opening on a plantar side of a bone in a foot;
forming a hole through the bone from a dorsal side of the bone to the plantar side to the opening in the plate;
inserting a fastener through the hole to the opening in the plate;
engaging a distal region of the fastener with the opening in the plate;
forming one or more additional holes through the bone from the dorsal side to the plantar side to one or more corresponding additional openings in the plate;
inserting one or more additional fasteners through the one or more additional holes to the corresponding additional openings in the plate; and
engaging a distal region of each of the one or more additional fasteners with the one or more corresponding additional openings in the plate to secure the plate to the plantar side of the bone only with the fastener and the one or more additional fasteners.

15. The method of claim 14, wherein the fastener and the one or more additional fasteners comprise screws having locking threads on their distal regions configured to engage with threads in the opening and one or more additional openings.

16. The method of claim 14, further including engaging a proximal region of the fastener with the bone on the dorsal side of the bone.

17. The method of claim 14, further comprising employing a guide pin to aid in forming the one or more additional holes.

18. The method of claim 14, wherein the fastener is inserted perpendicular to a longitudinal axis of the plate.

19. The method of claim 14, wherein the fastener is inserted at an angle to a longitudinal axis of the plate.

* * * * *